(12) United States Patent
Ostermeyer (10) Patent No.: US 8,908,179 B2
(45) Date of Patent: Dec. 9, 2014

(54) CUVETTE AND OPTICAL MEASUREMENT APPARATUS

(75) Inventor: Martin Ostermeyer, Gehrden (DE)

(73) Assignee: Anton Paar GmbH, Graz (AT)

( * ) Notice: Subject to any disclaimer, the term of this patent is extended or adjusted under 35 U.S.C. 154(b) by 122 days.

(21) Appl. No.: 13/422,316

(22) Filed: Mar. 16, 2012

(65) Prior Publication Data

US 2012/0236306 A1 Sep. 20, 2012

(30) Foreign Application Priority Data

Mar. 18, 2011 (DE) .................. 10 2011 005 807

(51) Int. Cl.
| | |
|---|---|
| *G01J 4/00* | (2006.01) |
| *G01N 21/03* | (2006.01) |
| *G01N 21/59* | (2006.01) |
| *G01N 21/21* | (2006.01) |
| *G01N 21/51* | (2006.01) |
| *G01N 21/64* | (2006.01) |

(52) U.S. Cl.
CPC ................ *G01N 21/21* (2013.01); *G01N 21/03* (2013.01); *G01N 21/51* (2013.01); *G01N 21/59* (2013.01); *G01N 21/645* (2013.01); *G01N 2021/0346* (2013.01)
USPC ............ 356/364; 356/246; 356/440; 422/500

(58) Field of Classification Search
USPC ................. 356/244, 246, 432–440, 364–369; 422/50, 500, 68.1
See application file for complete search history.

(56) References Cited

U.S. PATENT DOCUMENTS

| | | | | | |
|---|---|---|---|---|---|
| 3,157,727 | A | * | 11/1964 | Hardy et al. .................. | 356/368 |
| 5,082,790 | A | * | 1/1992 | Theobald et al. ............. | 436/536 |
| 5,894,733 | A | * | 4/1999 | Brodner ........................ | 62/51.1 |
| 6,793,624 | B2 | * | 9/2004 | Tsenkova ...................... | 600/309 |
| 8,671,783 | B2 | * | 3/2014 | Fuhr et al. .................... | 73/863.11 |
| 2004/0019462 | A1 | * | 1/2004 | Gehrlein et al. .............. | 702/188 |
| 2007/0014693 | A1 | * | 1/2007 | Kantrowitz et al. ............ | 422/99 |
| 2011/0149282 | A1 | * | 6/2011 | Wagner ......................... | 356/364 |
| 2011/0241883 | A1 | * | 10/2011 | Hamling et al. ........... | 340/572.8 |
| 2012/0137892 | A1 | * | 6/2012 | Dollner et al. .................. | 99/280 |
| 2013/0258336 | A1 | * | 10/2013 | Ostermeyer et al. .......... | 356/364 |

FOREIGN PATENT DOCUMENTS

CN 101424616 A1 5/2009

* cited by examiner

*Primary Examiner* — Hoa Pham
(74) *Attorney, Agent, or Firm* — Robert A. Blaha; Smith Risley Tempel Santos LLC (57) ABSTRACT

A cuvette comprising a cuvette wall for limiting a sample reception space for receiving a fluid sample is disclosed. The cuvette wall is adapted to allow a traversal of measurement radiation through the fluid sample situated within the sample reception space. An information presenter is fixed at the cuvette wall. The information presenter wirelessly provides data to be transferred to an external data reception module. The data to be transferred relates to the cuvette. Further, an optical measurement apparatus is described.

19 Claims, 4 Drawing Sheets

Fig. 4

CUVETTE AND OPTICAL MEASUREMENT APPARATUS

TECHNICAL FIELD

The present invention relates to a cuvette and to an optical measurement apparatus which comprises the cuvette.

In particular, the invention relates to a sample cell for an arrangement for measuring a temperature dependent optical characteristic quantity of a fluid sample in a polarimeter, which enables, by an encapsulated storage and/or measurement element at the cuvette, a simple handling upon installation in the polarimeter and a simple cleaning by providing a dish washer proof construction. The storage and/or measurement element (in the following also referred to as information presenter or information provider) comprises a sensor for a temperature measurement directly at the sample and/or means or a component for recognizing the employed cuvette/sample cell, wherein the specific geometry data and material data may be deposited at the cuvette and may thus be available automatically and without any help of the user.

BACKGROUND

A fluid sample may be received in an optically transparent cuvette and may be examined by radiating it using measurement radiating in an optical manner.

CN 101424616 discloses a device for keeping the temperature of a material constant which is optically examined. The device comprises an elastical clamp mechanism and two tubes, wherein a cross-section of each tube has a meniscus shape or an U-shape. A temperature measurement or temperature regulation is, however, not possible with sufficient accuracy.

There may be a need for a cuvette and for an optical measurement apparatus, wherein the above-mentioned problems are at least partially overcome. In particular, there may be a need for a cuvette and an optical measurement arrangement, which allow an accurate temperature measurement and/or a temperature regulation of a sample received within the cuvette during an optical measurement.

SUMMARY

According to an embodiment of the present invention a cuvette (in particular a vessel made of glass, plastic and/or steel with in particular transparent plane-parallel side faces or side walls) is provided which comprises a cuvette wall (in particular comprising several cuvette wall sections which are each planar) for limiting (in particular enclosing) a sample reception space (which has in particular a volume of 10 µl to 2000 µl) for receiving (a stationary sample or a flowing sample) a fluid (in particular liquid) sample (in particular an optically active sample which rotates polarized light with respect to its polarization plane), wherein the cuvette wall (in particular a first cuvette wall section and a second wall section which are arranged opposite to each other and which are in particular arranged parallel to each other) is adapted to allow a traversal (in particular a transmission) of measurement radiation (in particular electromagnetic radiation in an ultraviolet, visible and/or infrared wavelength range) through the fluid sample present or situated within the sample reception space. Further, the cuvette comprises an information presenter or information provider (which in particular provides static information or dynamic information, i.e. information which varies) for wirelessly (in particular optically and/or electromagnetically) providing data to be transferred which relates to the cuvette (which in particular relate to an identity of the cuvette, properties of the cuvette, such as a geometry of the cuvette or thermal properties of the cuvette or which relate to measurement data of a sensor, which is fixed at the cuvette) to an external data reception module (which is adapted to receive the to be transferred data wirelessly and contactlessly, in an optical and/or electromagnetic way), wherein the information provider is fixed at the cuvette wall (in particular at a cuvette wall section, which is not a cuvette wall section, which is not traversed or transmitted by the measurement radiation and thus is different from the first cuvette wall section and the second cuvette section), wherein the information provider is in particular liquid-tight and/or in a dish washer proof manner fixed at the cuvette wall such that the information provider is protected from external influences, such as solvent, water and/or dirt.

In particular, the information provider is fixedly connected with the cuvette wall and sustains a cleaning of the cuvette. The information on the information provider, i.e. the to be transferred data, may be actively transferred from the information provider. In other embodiments the information provider itself is passive and the to be transferred data are read-out from or by the external data reception module, without an active contribution of the information provider.

The to be transferred data may for example be used by or from an evaluation unit or processing unit of an optical measurement apparatus, to evaluate optical measurement data. In particular, the to be transferred data may comprise a traversal path length through the sample presently situated within the cuvette, temperature calibration values of the cuvette or other properties, in particular optical and/or geometrical properties of the cuvette, whereby an evaluation of optical measurement data is improved. Further, the to be transferred data of the information provider may comprise identification data for identifying the cuvette, wherein calibration data or geometry data associated with the identified cuvette may be held or stored in a storage which is accessible to the external data reception module and which thus also are available for an evaluation of optical measurement data.

The to be transferred data may be coded in any manner, for example as alphanumeric symbols, as a bar code, as a one-dimensional or two-dimensional pattern, in particular as a colour pattern.

According to an embodiment of the present invention the information provider comprises an optical pattern or pattern field (in particular an one-dimensional or two-dimensional bar code, a stripe code or a two-dimensional dimensional optical pattern which, for reading, exhibits in particular contrast in the ultraviolet, visible and/or infrared wavelength range), wherein the to be transferred data relating to the cuvette are coded in the bar code. The to be transferred data may be coded in any manner, in particular as alphanumeric symbols, as stripe code, as one-dimensional or two-dimensional pattern, in particular as a colour pattern. In this way static information which relates to the cuvette and which is unchangeable may easily be read-out from or by an optical reader device which is comprised in the optical measurement arrangement. The read information may be used for evaluating of optical measurement data, in particular to obtain an optical path length which has been traversed through the sample or/and to obtain temperature calibration data, to improve an accuracy of an optical measurement and evaluation of the optical measurement data of the sample.

According to an embodiment of the present invention the information presenter comprises a data transfer module (in particular comprising a processor and a coil) for electromagnetically (in particular wirelessly) transferring the to be transferred data. The data transfer module may comprise a transmitter for transmitting of electromagnetic waves. In particular, the data transfer module is adapted for wirelessly transferring or transmitting of the to be transferred data to the external data reception module, without involving current flow between the data transfer module and the data reception module and without involving an electric contact (between electrical conductors) between the data reception module and the data transfer module. Thereby, a reliable data transfer may be ensured, without requiring a fault-prone electrical contact. In particular, by the electromagnetic, wireless transfer of the to be transferred data, electrical contact problems may be circumvented.

The data transfer module may either comprise its own energy supply, in particular a battery or an accumulator, or may be adapted as a so-called passive data transfer module which does not have its own energy supply. The data transfer module may operate in an optical manner, in a capacitive manner, in an inductive manner or in any other manner which allows wireless, contactless transfer of the data.

According to an embodiment of the present invention the data transfer module is adapted for transferring the to be transferred data using radio frequency-technique (RF-technique), in particular ZigBee, WLAN and/or wireless USB, wherein the data transfer module in particular comprises an active (comprising its own energy supply) or passive (absent an energy supply) transponder (in particular a wireless communication device, which receives incoming signals and responds or forwards, wherein the transponder in particular comprises a transmitter and a responder). Thereby, WLAN refers to a wireless local area network and wireless USB refers to a wireless universal serial bus. Thereby, the data transfer module may be configured in a cost-effective manner. Further, the reliability of the data transfer may be ensured.

According to an embodiment of the present invention the data transfer module is adapted for optically transferring or transmitting (in particular in an ultraviolet, visible and/or infrared wavelength range of the electromagnetic spectrum) and/or for capacitively transferring (wherein the data transfer module in particular comprises an electrode at which a voltage is applied which is modulated according to the to be transferred data) the to be transferred data. In particular, the data transfer module may comprise a light source, such as a LED, to transfer the to be transferred data by modulation of the amplitude and/or modulation of the frequency of the light emitted by the light source, in particular to the external data reception module, which may thereby for example comprise a photodiode or a field of photodiodes. Thereby, a reliable data transfer may be assured.

According to an embodiment of the present invention the data transfer module is adapted for transferring the data to be transferred using ultrasonic sound.

According to an embodiment of the present invention the information provider comprises a sensor which is adapted for detecting a physical quantity relating to the sample and/or relating to the cuvette, in particular for detecting a temperature of the sample and/or detecting a positioning of the cuvette. Measurement data may thereby represent dynamic information which is transferrable from the information provider. In particular, the information provider may comprise a data transfer module as well as a sensor, both of which are fixed at the cuvette wall. Thereby, the sensor and the data transfer module may be integrated or may be constructed as separate elements, which are communicatively coupled, in particular or for example via one or more electric leads or electric conductors or electric wires.

The sensor may for example detect the temperature of the cuvette at the cuvette wall section at which the sensor is fixed. The temperature of the fluid sample present within the sample reception space may further be derived using temperature calibration data which may also be provided from the information provider.

For determining the positioning of the cuvette, for example in a sample holder or a cuvette holder of an optical measurement apparatus, the sensor may for example determine in an optical way a position of a label or a marker at the cuvette holder relative to the position of the sensor and may, based upon that, determine or derive, whether the cuvette is correctly positioned or whether deviations to a correct positioning of the cuvette are present. Thereby, the evaluation or determination of a correctness of the cuvette positioning may either be performed by the information provider (in particular a processor) or by the external data reception module after transferring the to be transferred data. When the cuvette is not correctly positioned within the cuvette holder, the optical measurement apparatus may for example output a warning message for the user. Thereby, an improvement of the optical measurement is enabled.

In particular, during an operation or during using the cuvette in an optical measurement apparatus, the cuvette and thus also the sample present within the cuvette may be heated or cooled (in particular tempered), for example using a Peltier element or a water bath, wherein the temperature and/or a change of the temperature of the sample or the cuvette wall may continuously or in a sampled manner be monitored using the temperature sensor. Thereby, for example optical properties of the sample may be examined depending on the temperature.

According to an embodiment of the present invention the data relating to the cuvette comprise an identification of the cuvette (such as an ID of the cuvette, which unambiguously identifies the cuvette) and/or a geometry of the cuvette (in particular a traversal length of the sample and/or a volume of the sample reception space) and/or a material of the cuvette wall (such as glass, quartz glass or plastic, in particular the type of the glass) and/or calibration data of the sensor (in particular temperature calibration data for determining the temperature of the sample from the measurement data of the temperature sensor). Thereby, optical measurement data may be evaluated or processed in a simple manner and in an improved manner.

According to an embodiment of the present invention the information presenter comprises an electronic storage (in particular comprising a semiconductor material) which is adapted for storing storage data and which (as a component of the information presenter) is fixed at a section of the cuvette wall, wherein the to be transferred data comprise at least a portion of the storage data. Storage data may represent static information, which is independent of physical conditions, such as temperature, of the cuvette. Nevertheless, the storage data are changeable by writing or modifying.

In particular, the electronic storage may comprise a storage capacity between 8 byte and 1 Mbyte, in particular 100 byte and 10 kbyte.

In particular, the information presenter may comprise a data transfer module as well as a sensor as well as an electronic storage.

Thereby, further (in particular from outside changeable, via a writing device) properties of the cuvette may be stored within the electronic storage and these further properties may be transferred as required or as needed to the external data reception module of the optical measurement apparatus, to refine an evaluation of the optical measurement data.

According to an embodiment of the present invention the cuvette further comprises a reception module for electromagnetically (in particular wirelessly, contactlessly) receiving the to be received data and/or for receiving electrical energy. The reception module may comprise a coil (in particular comprising a wound electrical wire), in order to receive the to be received data and/or the to be received electrical energy using induction.

In particular, the to be received data may be sent or transmitted during a manufacturing or after measuring or surveying the cuvette to the reception module and may be stored within the electronic storage. The to be received data may in particular include an identification information of the cuvette, geometry information of the cuvette and/or calibration information, in particular temperature calibration information of the cuvette. Further, the to be received data may be provided for programming (in particular of a processor, which may be comprised in the information provider). In particular, the cuvette may be adapted for transmitting of to be transferred data and for receiving of to be received data, to thus enable a bidirectional communication between the cuvette and one or more modules of an optical measurement apparatus. Thereby, an optical measurement of the sample may further be improved.

According to an embodiment of the present invention the cuvette is adapted, in particular the reception module is adapted, to receive the electrical energy using RF-technique, in particular ZigBee, WLAN, and/or wireless USB and/or to receive the energy optically. For an optical reception the cuvette may in particular comprise a photodiode, to generate from an optical signal, which may for example be emitted from the optical measurement arrangement or apparatus, electrical energy. In particular, the cuvette may comprise an energy storage element, such as a capacitor or an accumulator. Thereby, the performance of the cuvette may further be improved.

According to an embodiment of the present invention the cuvette is adapted to write at least a portion of the received data into the storage element. In particular, updated calibration data after certain operation time ranges or in dependence of a used tempering apparatus may be written into the storage element.

According to an embodiment of the present invention the cuvette wall (in particular two cuvette wall sections being arranged opposite to each other, which may in particular oriented parallel to each other) is along an optical axis (which may be in particular perpendicular to the plane faces of the two cuvette wall sections) at least to 70%, in particular at least for 80%, transparent for the measurement radiation which comprises a wavelength in at least a portion of a wavelength range between 300 nm and 1000 nm, in particular between 400 nm and 800 nm. Thereby, in particular, the measurement radiation is attenuated in at least a portion of the abovementioned wavelength range at most by 20% or 30% in its intensity upon traversal along the optical axis through the two cuvette wall sections. Thereby, losses of measurement radiation may be reduced, because of which as a light source for generation of the measurement radiation a moderately intensive light source may be sufficient.

According to an embodiment of the present invention the cuvette is adapted as a through flow cuvette, wherein the cuvette comprises an inlet connector/connection or inlet terminal and an outlet connector/connection or outlet terminal. Thereby, the inlet connector and the outlet connector are arranged and adapted, to allow an inflow of the (in particular liquid) sample from the inlet connector into the sample reception space, to allow a traversal or flow-through of the sample through the sample reception space to the to the outlet connector and to allow a discharge or outflow of the sample from the outlet connector. Thereby, the cuvette may be supplied with a continuous stream or flow of a sample and an optical measurement may be provided, to for example allow an optical analysis of an eluate of a chromatography column or of a (bio)chemical separation column.

According to an embodiment of the present invention the information provider (which in particular comprises the data transfer module and/or the sensor and/or the electronic storage and/or the reception module) is liquid-tight (to protect the information presenter from a contact with a liquid) encapsulated at the cuvette wall (such as injection moulded, encased or tightly cladded, encapsulated or enclosed). Thereby, a reliable operation of the information presenter may be assured, in particular when the information presenter comprises one or more electronic components.

According to an embodiment of the present invention the information presenter is encapsulated or embedded (for example moulded, or inserted, such as inserted in glass) within a cuvette wall material. In particular, optically transparent glass, such as Duran®, may be used also or also quartz glass or special glasses, which are suitable for infrared applications, UV-applications or applications of visible light. Duran is the registered trademark of Schott AG of Mainz, Fed. Rep. Germany.

According to an embodiment of the present invention the information presenter is fixed at or on the cuvette wall using an embedding material or moulding material (in particular a chemically inert embedding material, such as resin, in particular artificial resin) and/or using a coating or cover (in particular a shrink foil or shrink wrap or an arbitrary plastic foil which is tight and durable and stable) and/or using welding (in the case of a metal cuvette, such as a stainless steel cuvette or a metal cuvette manufactured from a non-magnetic material). The information provider may also be screwed at the cuvette wall, may be soldered or may be fused. Thereby, a reliable fixation of the information provider (in particular comprising the data transfer module and/or the sensor and/or the electronic storage) is assured.

According to an embodiment of the present invention the information presenter is fixed at the cuvette wall such that the fixation sustains a cleaning using a tenside containing solution of a concentration between 0.5 wt % and 10 wt %, in particular 2 wt % and 3 wt %, at a temperature between 60° C. and 95° C., in particular between 80° C. and 95° C., during a time range between 2 min and 30 min, in particular 15 min and 30 min. In particular, the cuvette may be subjected to a cleaning which corresponds to the conventional CIP (Cleaning In Place) cleaning procedure for food products, without impairing the fixation of the information presenter. The tenside containing solution may for example comprise NaOH and/or $HNO_3$. Thereby, the cleaning may also cause a disinfection, wherein the cuvette may be subjected to a (e.g. water containing) steam for example, which may have a temperature up to 120° C. or less. Due to the cleaning the cuvette may be made sterile, without deteriorating a fixation and/or an integrity of the information presenter. A CIP-cleaning which does not deteriorate a duration or a stability of the fixation of the information provider may for example comprise a pre-cleaning, or a pre-rinsing, to remove crude or gross contamination; a cleaning using a basic or alkaline material or chemical; a rinsing using water; an acid washing to remove chalk deposits; a rinsing using water; a disinfection for killing of vegetative microorganisms; a rinsing of the disinfection material and a final rinsing with ultrapure water.

Further, the fixation of the information provider may be dish washer proof, wherein laboratory dish washers may reach a cleaning temperature of 95° C. In particular, the cuvette may be resistant to a base and resistant to an acid, wherein the cuvette may support the entire PH range, wherein the borders are covered with Hastelloy® and glass, as well as PTFE-cuvettes. Thereby, a very reliable stable and resistant cuvette for the laboratory laboratory operation may be provided. Hastelloy® is the registered trademark of Haynes International, Inc. of Kokomo, Ind., U.S.A.

According to an embodiment of the present invention an optical measurement apparatus (for optically measuring a fluid sample) is provided which comprises a radiation source (such as a laser, LED, a high-pressure lamp, a halogen lamp or the like) for generating measurement radiation (which may in particular be linearly or circularly polarized and which may lie in the ultraviolet, visible and/or infrared wavelength range); a cuvette according to one of the afore-mentioned embodiments, which is arranged in a radiation path or beam path of the measurement radiation; a measurement radiation receiver (such as a photodiode, a field of photodiodes, a CCD-camera, a CMOS-sensor, a line detector or matrix detector, a photomultiplier, Avalanche photodiodes etc.), which is arranged and adapted for detecting of intensity values of the measurement radiation, which has traversed through the sample reception space (and through the sample present therein) of the cuvette; a data reception module which is adapted for receiving the data of the information presenter which data relate to the cuvette; and an evaluation unit which is adapted to evaluate the intensity values of the measurement regulation based on the received data which relate to the cuvette, in order to determine an optical property (in particular an optical activity, such as a rotation angle of a rotation of a polarization direction of the measurement radiation upon transmission through the sample) of a sample situated within the sample reception space.

Between the information provider and the data reception module an electrical isolator (such as air, plastic, etc.) may be arranged, wherein the information presenter and the data reception module may be electrically separated and isolated from each other.

The optical measurement apparatus may comprise optics for focusing and/or shaping the measuring radiation. Further, the optical measurement apparatus may comprise one or more polarizers, in order to generate measurement radiation of a particular polarization or of a particular polarization state, such as a linear polarization state (in particular using a first polarizer upstream of the sample or of the cuvette) and in order to analyze the measurement radiation having traversed through the sample regarding its polarization state (using a second polarizer downstream of the sample or the cuvette).

The optical measurement apparatus may be adapted as an absorption measurement apparatus, as a fluorescence measurement apparatus or as a scattering measurement apparatus.

In particular, the optical measurement apparatus may be adapted as a polarimeter and may comprise a polarization filter as polarizer, in order to polarize, in particular to linearly polarize impinging measurement light which impinges in a parallel manner or to polarize impinging measurement radiation which impinges in a parallel manner. As polarization filter for example a Nicol prism, a Glan-Thompson-Polarizer or a Tourmaline piece or plate may be employed. After traversal of the measurement radiation of a defined polarization state a polarization plane of the measurement radiation may be rotated due to the optical activity of the sample situated within the cuvette. This occurs when using so-called optically active compounds or materials. In order to determine a rotation value $\alpha$ of the rotation of the polarization plane due to the traversal of the measurement radiation through the sample, the measurement radiation traverses after traversal through the sample a second polarization filter which is also denoted as an analyzer. The analyzer is turned or rotated such that a possibly complete extinction or attenuation of the intensity of the measurement radiation is detected at the measurement radiation receiver.

In the case in which the information presenter of the cuvette comprises an optical pattern or a bar code at the cuvette wall, the data reception module may comprise a light source, in order to illuminate the bar code. The light backscattered from the bar code may be detected by the data reception module, whereupon the information contained therein may be derived. The data reception module may receive the to be transferred data provided by the information presenter wirelessly and contactlessly. The receiving may thereby occur in an optical manner or upon using a RF-technique.

The evaluation unit may for example use an identification information, which is obtained from the data reception module, to determine properties of the cuvette regarding geometry, calibration, etc. using a look-up table. Alternatively, the evaluation unit may obtain data which relates to the geometry, the calibration or the like of the cuvette directly from the data reception module which has received the data from the information provider of the cuvette. Further, the evaluation unit may for example obtain temperature data from the data reception module, which data the data reception module has received from the information presenter.

According to an embodiment of the present invention the optically characterizing parameters of a sample, such as the extinction or the optical activity, may be determined via the change of electromagnetic radiation in the UV, VIS or NIR range by directing light onto the sample situated within the sample cell and by analyzing the change of the (light) beam having interacted with the sample. The arrangements or configurations of the beam guidance may thereby vary, measurement cells or cuvettes for transmission or reflection are possible as well as for example ATR-cells (Attenuated Total Reflection).

Optical activity refers to the property of chemical compounds, in the solid state or in solution, to rotate the plane of the polarized light upon transversal or transmission therethrough by a characteristic value (rotation angle) characteristic for the respective compound. Optically active compounds each exist in two isomers from which one isomer rotates the plane of the polarized light to the right-hand side (indicated by + or d), the other isomer rotates to the left-hand side (labelled by – or l). Optical isomers behave regarding its formulas and its crystals like image and mirror image. The majority of the optical active compounds have one or more asymmetric carbon atoms.

Optically active substances play a big role in many research fields, in particular in research and production of chiral molecules in the chemical and pharmaceutical industry, in the food industry (for example for characterizing of sugar and starch) through to monitoring and regulation of physical, chemical and biotechnological processes.

According to an embodiment of the present invention the optical measurement apparatus is adapted as a polarimeter, wherein the optical property of the sample is indicative for the optical activity of the sample. The polarimeter may for example comprise a light source, a polarizer, the cuvette, an analyzer and a detector, which are arranged and adapted, to measure an optical activity of the sample, for example a rotation angle $\alpha$ of a rotation of polarization plane.

Thereby, the measured rotation angle α may be proportional to the concentration of the sample which may be to be determined. Further, the measured rotation angle α may depend on the temperature of the sample. In order to correctly determine the concentration of the sample, the temperature of the sample thus needs to be sufficiently accurately known. The temperature of the sample may be measured using a temperature sensor which is fixed at the cuvette wall of the cuvette, may be transferred from the cuvette to the data reception module and may be taken into account during the evaluation of the optical measurement data. Thereby, an improved optical measurement of the sample is enabled.

According to an embodiment of the present invention the optical activity of a substance is measured using the optical measurement apparatus which is in particular adapted as polarimeter.

For determining the rotation angle α the to be examined sample is arranged between two polarization filters (Nicol prism, Glan-Thompson-Polarizers or Tourmaline pieces or the like). In the first filter (polarizer) the parallel impinging light is polarized. When the second filter (analyzer) is arranged 90° relative to the polarizer, no light traverses. When now the optically active substance (the fluid sample) is arranged between the two filters, the sample rotates the polarization direction of the traversing light and the analyzer or the polarizer may be re-adjusted by an angle, in order to again achieve extinction or cancellation (at the detector). This rotation angle α is proportional to the rotation ability of the substance and to its concentration.

According to an embodiment of the present invention a polarimeter is provided in which the analyzer consists of a polarization beam divider and two detectors, which measure the orthogonal polarization components after traversal or transmission of the measurement regulation through the sample. Polarizer and/or analyzer are then turned or rotated relative to each other such that both polarization components are in a predetermined ratio (typically they are equal or have the same magnitude). This rotation angle is again proportional to the rotation ability of the substance and to its concentration.

According to an embodiment of the present invention a polarimeter is provided in which no optical element is turned or rotated, but wherein the rotation of the polarization plane caused by the optical activity of the sample is compensated using an optical element, typically a Faraday rotator which comprises a coil. For a Faraday rotator the rotation of the polarization plane is proportional to the electrical current flowing through the coil of the Faraday rotator. The current necessary for compensating of the rotation caused by the sample is proportional to the rotation ability of the substance and its concentration.

According to an embodiment of the present invention a polarimeter is provided in which either the analyzer and/or the polarizer are continuously rotated (in particular relative to each other). The phase shift of the evolving intensity modulation of the detector is proportional to the rotation ability of the substance and its concentration.

The polarimeters are generally adjusted or calibrated using quartz control plates having known thickness and/or rotation value. Also these quartz control plates may be provided with the embodiments of the present invention, beside the thickness of the quartz plate and/or rotation value for the specific wavelength additional secondary information like serial number, data of the calibration, number of the calibration sheet, certificate data etc. may be provided on the information presenter.

According to an embodiment of the present invention the received data relating to the cuvette comprise temperature data of the sample, wherein the evaluation unit is adapted, to determine the optical property of the sample taking into account the temperature data of the sample. Further, the evaluation unit may be adapted, to determine a concentration of the sample based on the optical measurement data and the temperature data.

According to an embodiment of the present invention the optical measurement apparatus further comprises a Faraday modulator (a special form of polarization filter which is adapted to generate a magnetic field) for changing a polarization direction of the measurement radiation, wherein the cuvette is adapted, to receive energy from an electromagnetic field generated by the Faraday modulator. Thereby, a separate hardware for transferring energy to the cuvette may be dispensed therewith.

According to an embodiment of the present invention the optical measurement apparatus further comprises a pyrometer which is arranged and adapted for detecting the temperature of the cuvette and which is communicatively coupled with the evaluation unit. Thereby, the pyrometer may determine the temperature of the cuvette by receiving of infrared radiation from the cuvette. In this case a temperature sensor at the cuvette is not necessary.

According to an embodiment of the present invention the cuvette is adapted to modulate the data relating to the cuvette onto or upon the measurement radiation and the evaluation unit is adapted for demodulating the modulated measurement radiation, in order to extract the data relating to the cuvette.

Features of embodiments of the cuvette individually and/or in combination disclosed may also be applied to the optical measurement apparatus and features regarding embodiments of the optical measurement apparatus individually or in combination disclosed may also be applied to the cuvette.

BRIEF DESCRIPTION OF THE DRAWINGS

Embodiments of the invention are now described and explained referring to the accompanying drawings. The invention is not limited to the described or illustrated embodiments. Similar elements (in structure and/or in function) in the different figures are denoted with similar reference signs which may differ only in the first position.

DESCRIPTION OF EMBODIMENTS

Figure 1:
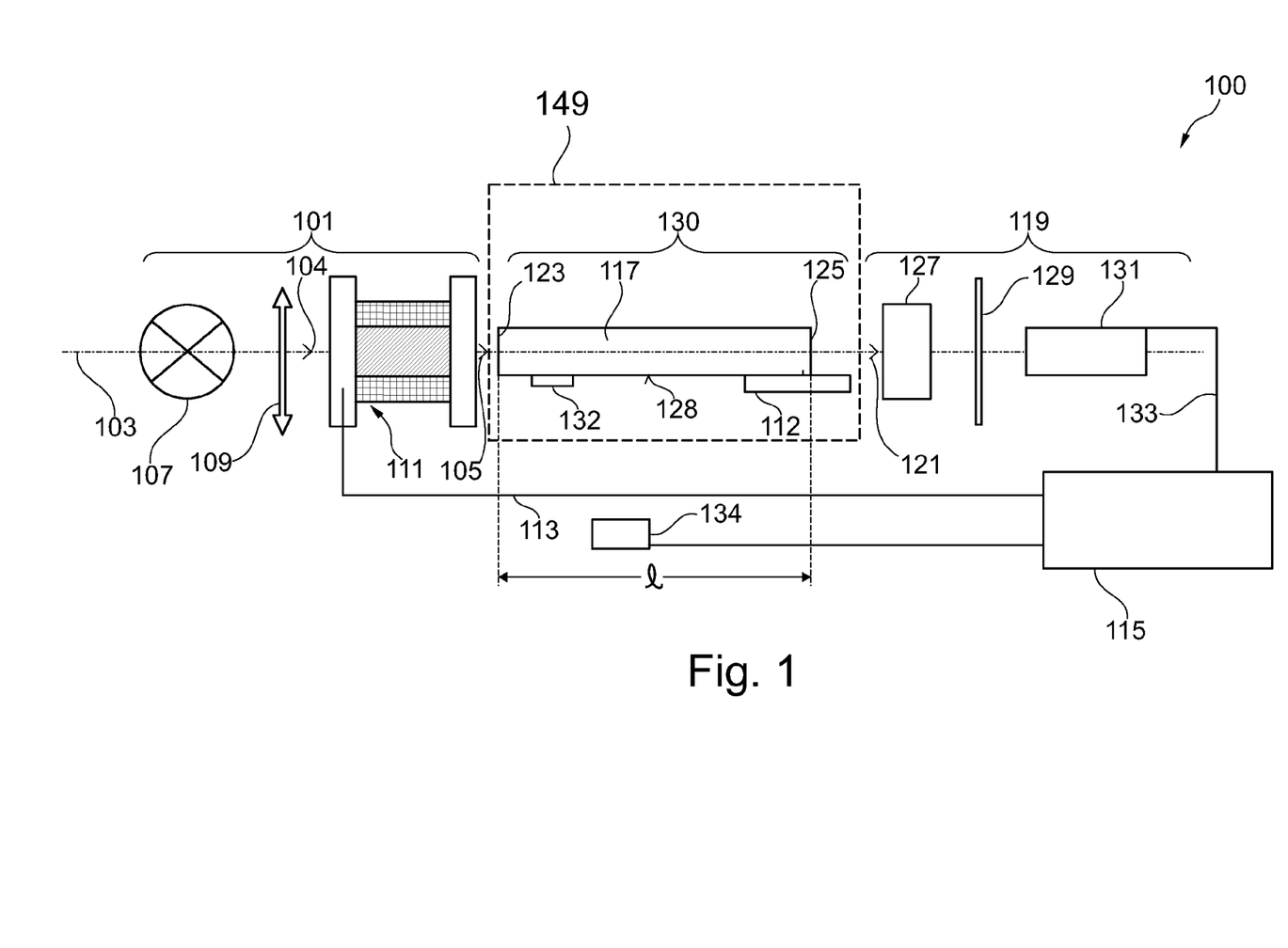
FIG. 1 shows an optical measurement apparatus according to an embodiment of the present invention, which comprises a cuvette according to an embodiment of the present invention.

FIG. 1 schematically shows an optical measurement apparatus 100 according to an embodiment of the present invention with polarization modulation, wherein the measurement arrangement is configured as a polarimeter. The optical measurement apparatus 100 comprises a section 101 for generating of measurement radiation which propagates along an optical axis 103. In particular, the measurement radiation 105 is generated using a light source 107 after which its traverses through a polarizer 109 which converts the measurement radiation generated by the light source 107 into linearly polarized measurement radiation 104. Thereby, an electrical field vector of the measurement radiation 104 runs along a particular direction which stands perpendicular to the optical axis 103. The measurement radiation generation section 101 of the optical measurement apparatus 100 further includes a Faraday modulator 111, which comprises a coil, in order to rotate the polarization direction of the measurement radiation 104 depending on an electrical current flowing through the coil by an angle about the optical axis 103 and in order to generate measurement radiation 105. For this purpose the Faraday modulator 111 is connected via a data line 113 with a processing and control system 115.

The optical measurement apparatus 100 further comprises a cuvette 130, in which a sample 117 is contained, which is in particular liquid and which in particular exhibits an optical activity. A cuvette assembly 149 comprises the cuvette 130, an information presenter 132 and a positioning arrangement 112.

The optical measurement apparatus 100 further comprises an analysis section 119, in order to analyze the measurement radiation passing through the sample 117 within the cuvette 130. The cuvette 130 including the sample 117 contained therein is arranged in the optical axis 103 or in the radiation path of the measurement radiation using a measurement cell holder (not shown), for example using or by means of positioning arrangements 112 and/or standard connections such as flange connections or thread connections such that the sample 117 is irradiated through windows 123 and 125 in the cuvette 130 across a length l (e.g., 0.1 mm-20 cm) by the measurement radiation 105. In the case the substance or sample 117 present within the cuvette 130 exhibits an optical activity, the polarization direction of the measurement radiation 105 is rotated, to generate the measurement radiation 121 with rotated polarization direction.

The analysis section 119 of the optical measurement apparatus 100 comprises an optical element 127, an analyzer or polarization filter 129 and a detector 131 which is connected via a data line 133 with the processing and control system 115. After loading or filling the sample 117 into the cuvette 130 the traversing or traversed measurement radiation 121 is detected or registered by the detector 131 and the current through the coil of the Faraday modulator 111 is changed by the processing and control system 115, until the intensity of the measurement radiation 121 transmitted through the sample 117 which reaches at the detector 131 is minimal.

According to other embodiments of the present invention either the polarizer 109 and/or the analyzer 129 is rotated using a motor or a stepping motor, to compensate the polarization direction of the measurement radiation 105 changed due to the sample 117, to detect minimal intensity values at the detector 131, which correspond to the intensity values which are obtained, if polarizer 109 and analyzer 129 (without inserted cuvette 130) exhibit crossed orientations (90° relative to each other), which cause minimal or no light transmission or light passage.

For temperature measurement and for identification of the cuvette 130, the cuvette 130 comprises an information presenter 132 which provides data relating to the cuvette for transferring to a data reception module 134, as is in more detail described with reference to FIGS. 2, 3 and 4. The information presenter 132 therefore comprises in particular a temperature sensor, which is adapted to measure the temperature of the cuvette 130 at the cuvette wall 128 at which the information presenter 132 is fixed. Temperature values are then transferred from the information presenter 132 to the data reception module 134, which in turn forwards the temperature values and/or identification information and/or geometry information of the cuvette 130 and/or calibration information to the processing and control system 115.

The measurement of the rotation angle $\alpha$ may be performed with an angle measurement device, typically an optical encoder, which is rigidly connected to the rotated optical element. Alternatively, the steps propagated by the stepping motor may be used for angle measurement if low accuracy requirements are set.

For a more accurate control of the optimal rotation a Faraday modulator, as indicated in FIG. 1 by reference sign 111, may be employed. The Faraday modulator 111 utilizes the property of some solid materials to become optically active upon applying magnetic fields. A bar of such a solid material is wrapped with an alternating current coil and the polarization direction of the optically active bar is periodically switched using an induced magnetic field, wherein the oscillation around the equilibrium point may be accurately determined using special evaluation algorithms. In FIG. 1 the Faraday modulator 111 is employed in connection with the light source 107 and the polarizer 109 for the generation of linearly polarized measurement light 105.

Embodiments of the optical measurement apparatus are not limited to the embodiment illustrated in FIG. 1 and in particular the cuvette 130 with information presenter 132 is employable in differently configured optical measurement apparatuses. Different optical measurement arrangements are provided which determine the optically characterizing parameters of a fluid medium 117 from the change of the properties of the electromagnetic radiation 105 upon traversal through the cuvette 130 filled with the sample 117 or a flow through cuvette or through flow cuvette.

The processing and control system 115 may be integrated in the optical measurement apparatus or polarimeter 100 and may be equipped with an input unit, such as for example a keyboard, data storage and data processing/program logic and an output unit and may be operated also externally via a computer and/or via an interface for data transmission.

The rotation value or rotation angle quantitatively depends on the structure of the optically active compound, on the layer thickness l of the irradiated sample and, for dissolved compounds, on the concentration c of the sample. In case of pure liquid the density ρ is used instead of c. Further factors are the wavelength of the used light, the temperature of the sample and potentially the properties of the solvent. The specific rotation value is a material constant. The specific rotation value or the specific rotation corresponds to the rotation angle for a concentration of 1 g/ml and a layer thickness of 1 dm. The wavelength and the temperature are indicated as indices of the measurement value.

$$[\alpha]_\lambda^T = \frac{\alpha}{c \cdot l} \quad \text{Equation 1}$$

where,
$\alpha$: the measured rotation angle [°]
c: concentration of the sample [g/l]
l: length of the cuvette [dm]
T: temperature [K]
$\lambda$: wavelength Thus, for the specific rotation value it evolves a dimension of [° ml*dm$^{-1}$ g$^{-1}$] or [° C. 10$^{-1}$ cm$^2$ g$^{-1}$]. Often the indication of the specific rotation value is indicated for a wavelength of λ=589.3 nm and at 20° C.

Depending on the measurement task different measurement wavelengths may be used. Standard wavelengths are for example 325 nm, 365 nm, 405 nm, 435 nm, 546 nm, 579 nm, 589 nm, 633 nm and 880 nm, which are used using different sources and/or appropriate filters for the measurement. The measurement of the rotation value for different wavelengths allows also the determination of the optical rotation dispersion (ORD). Often, for example the natrium-D-line (which doublet lies at 589 nm) is utilized, which is mainly established because of the easily available light source (Linnemann burner).

To achieve highest resolutions and accuracy across the entire measurement range different arrangements in the polarimeter based on the principle of the measurement are utilized, for example the utilization of Faraday modulators and Faraday compensators or Fourier analysis for determining the actual rotation angle. For the Fourier analysis, for example, a polarizer/analyzer is continuously rotated and the phase shift is measured using Fourier analysis (or lock-in technique).

Particular standards for example ICUMSA O.I.M.L. etc. require for the precise measurement of the optical activity, beside the accurate measurement of the rotation angle of liquid, also the exact knowledge of the sample temperature which is determined according to embodiments of the invention and which may be transferred to the system 115. Also the length of the used cuvette may be transferred using the information provider 132. To enable an accurate temperature compensation, it is necessary, to take the length expansion coefficient of the cuvette material into account. The loading of the cuvette with the sample 117 should as possible be performed without introducing bubbles and should be performed in a homogenous way.

The cuvette may be chemically inert and may be easy to load and may be easy to clean. Further, and simultaneously handling errors, for example, the choice of the wrong cuvette data, may be prohibited and also the calibration using the choice of the wrong calibration standard must not lead to errors.

The cuvettes employed in the polarimeter for examining of fluid samples may be made according to embodiments from glass, quartz glass or for example stainless steel, flow through cuvettes are utilized as well as individual tubes, which are separately loaded for individual measurements.

The measurement within the polarimeter is performed along a radiation path 103 through the cuvette parallel to the optical axis 103. Special arrangements for bubble-free loading and economical or most economical usage of the to be measured substance may be employed, while simultaneously a sufficient measurement stretch through the substance is assured.

The temperature measurement is performed via the temperature sensor in the information provider 132 and is further processed within the processing and control unit 115. Based thereon a control of the sample temperature may be performed using heating/cooling arrangements (not illustrated) within the sample chamber.

The tempering may for example be performed using a water bath surrounding the cuvette 130 and the temperature of the same (after sufficient waiting time for temperature equilibration) may be manually or automatically stored as sample temperature. When the sample space and/or the cuvette 130 is tempered using a Peltier element, the temperature measurement or the temperature sensor may be attached at or on the cuvette wall 128. With this value also the desired target temperature in the polarimeter 100 is potentially regulated or adjusted. Thus, the temperature determination does not occur in the tempering unit surrounding the measurement cuvette or in sensors mounted in the confined sample chamber, but directly at the cuvette wall 128, in order to achieve an improvement of the accuracy.

To meet highest requirements in a laboratory operation, cuvettes with integrated temperature sensor may be utilized. Thereby, the temperature is measured as close as possible to the sample and is stored within the processing and control or evaluation unit 115. For highest requirements the temperature sensors may generally be calibrated or adjusted and the calibration data evolving therefrom must be associated in an accurate and reliable manner to the respective cuvette in the evaluation unit 115.

According to embodiments of the invention it is proposed (see FIGS. 1 to 4), to effect the transfer between the evaluation unit 115 of the polarimeter and the temperature measurement by the sensor at the cuvette 130, 230, 330, 430 and/or an identification or as required the stored cuvette data to be at least section-wise contactlessly. Thereby, the portion on the cuvette 130, 230, 330, 430 required for the measurement and storage element for the data storage and temperature measurement may be constructed or designed in an encapsulated manner. Thereby, the manner of the wireless data transfer only plays a minor role, opportunities or possibilities of the data transfer for short transfer distances are e.g.:

RFID optically using LED/laser and photodetector optically using bar code for the stored data, temperature measurement also optically (pyrometer)

usage of ultrasonic sound, via the air or transfer through the cuvette holder

Both, the current temperature as well as an identification of the respective measurement cuvette 130, 230, 330, 430 may be contactlessly read and may as required serve as control parameters for the tempering arrangement. Moreover, these data are provided as error-free documentable measurement conditions for the determined rotation values. Thereby, reliable and completely documented results are achieved by a fully automatic and digital, objective and fast measurement.

When the cuvette is put onto the holder arrangement/mounting bars, the storage and evaluation unit of the polarimeter recognizes the cuvette resting thereon via the transmitter module present within the sample chamber. The data transfer may be performed using wireless/electromagnetic/RFID but also optically/IR.

By a simple encapsulation of the required sensor and electronic component residing at the cuvette, a robust, easy to handle and protected against operation or handling errors, dish washer proof cuvette may be manufactured.

Thereby, at least one label or characterization and/or a sensor for monitoring the temperature may be associated with the cuvette. Further, a reception or receiving unit 134 is provided in the optical measurement arrangement to which data are wirelessly or via an air transfer path or air conduction path transferrable.

The data of the cuvette may be resident in respective readable form, for example in an electronically readable form or in optically recognizable form at or on the information provider 132, 232, 332, 432 of the cuvette. The deposition of the data or the programming of the storage may occur using arbitrary means, normally this may occur during a manufacturing process or a maintenance process. The data deposited or resident at the storage of the information provider 132, 232, 332, 432 of the cuvette may be the calibration data of the temperature sensor as well as information regarding the used cuvette and may be provided during the polarimeter operation via the chosen contactless communication opportunity. When desired also the communication with the storage may occur via this transfer way in a bidirectional manner.

The temperature measurement may be performed in a contactless technique.

Ideally the data transfer may be established, when the cuvette is correctly placed within the measurement cell holder which may be also detected. Thereby, a further issue for quality assurance may be met: "recognizing the correct position of the measurement cell". This may, for example, occur by an additional control of the position of transmitter and receiver relative to each other.

Generally, the used temperature sensors may require energy for the measurement, which may also be contactlessly coupled. When using active transmitters the energy supply may be present or included, for example an integrated battery or accumulator. Also in the case of a wireless energy transfer there are different possibilities which are combinable with the variants of the signal transfer in an arbitrary manner.

The energy transfer may occur inductively, with classic RFID with separate coil, besides also for the utilization of a Faraday coil for modulation of the polarimeter measurement signal its parasitic emerging magnetic field may be used for energy supply (conventionally this parasitic field is shielded).

When using a normal radio transmitter and having a sufficiently small distance, also a strong transmitter may serve for the energy supply. In case of an optical solution the energy supply for the sensor may also be optically performed.

The cuvette illustrated in FIGS. 1 to 4 may be configured as flow through cuvettes as well as loading cuvettes with or without tempering arrangements.

Figure 2:
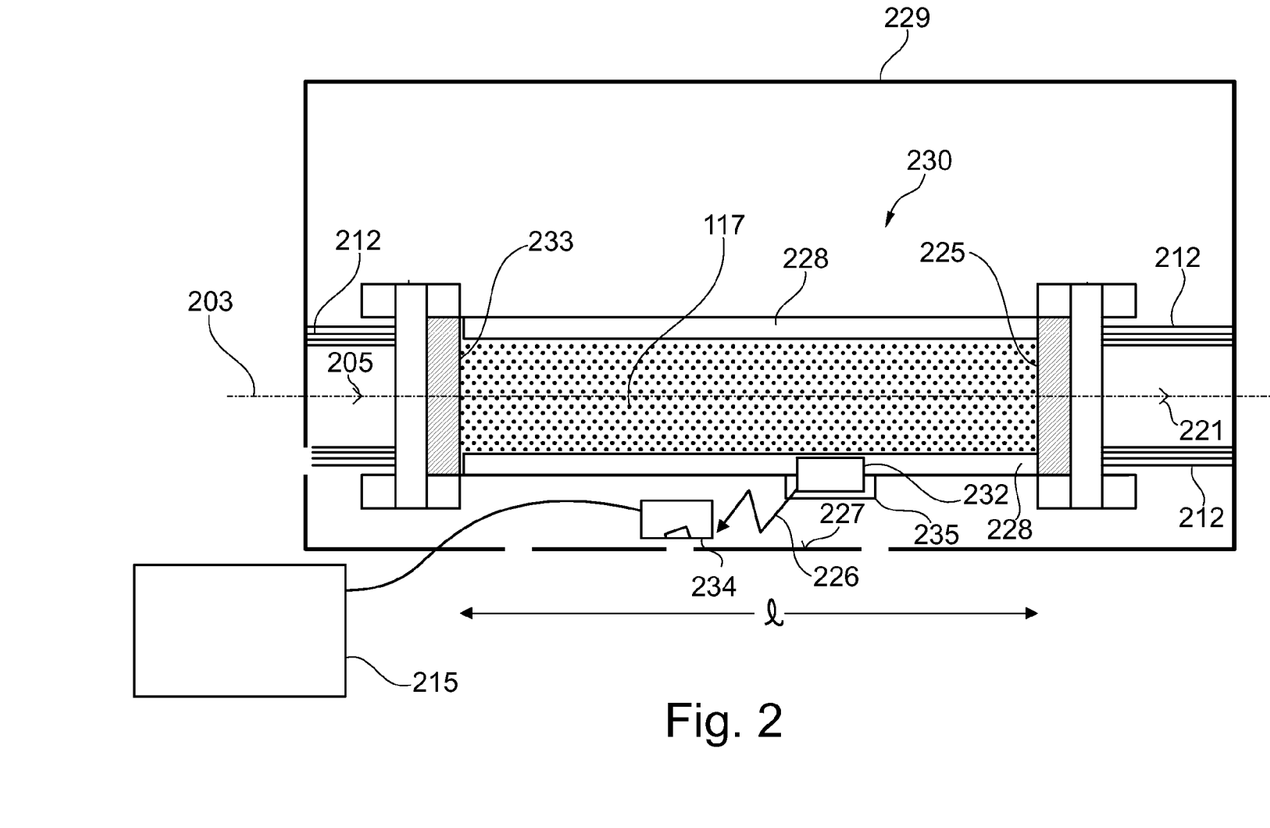
FIG. 2 schematically illustrates a cuvette according to an embodiment of the present invention which may be in communication with components of the optical measurement apparatus as it is for example illustrated in FIG. 1.

FIG. 2 schematically shows a cuvette 230 according to an embodiment of the present invention. In this embodiment, the cuvette 230 utilizes the radio-frequency-identification-technology (RFID-technology), which for example is broadly used for identification of articles and which takes advantage of components which are economically available on the market.

In the embodiment shown in FIG. 2 the cuvette 230 is adapted as a cuvette without a tempering cladding or tempering coat. The tempering may be realized by separate tempering apparatuses (not shown) of the polarimeter or the optical measurement apparatus 100 illustrated in FIG. 1, such as Peltier elements, by an electrical heating or also by separate water tempering.

The information presenter 232 is fixed at the cuvette wall 228 of the cuvette 230, in particular fluid-tightly encapsulated using a glass encapsulation 235. In particular, the information presenter 232 comprises a storage and measurement unit for measuring the temperature of the cuvette 230 and for storing of data relating to the cuvette and/or storing of data relating to a temperature calibration. The encapsulation may occur during the manufacturing process of the cuvette 230 using the material of the cuvette (quartz, glass, metal), however, the ecapsulation may also be constructed or designed as a coating. For the coating or layering for example plastic(s) or a foil may be applied onto the cuvette, which liquid-tightly surround the information presenter 232 and encapsulate the information presenter 232 and which are sufficiently resistant against the required cleaning steps. The coating may, for example or in particular, enclose the cuvette entirely or may merely cover a fractional portion of the cuvette wall 228.

The information presenter 232 which comprises the storage and measurement unit contains a sensor element for measuring a physical quantity which is related to the temperature of the cuvette or the temperature of the sample 117, wherein the sensor supplies the measurement data in form of electrical signals. The information presenter 232 further comprises a storage module, in particular an electronic storage module, in which data for the used cuvette (in particular geometry data, such as length, diameter, used material or the like) as well as, as required, calibration data or alignment data for the temperature sensor may be stored, in particular at the factory in a non-volatile manner.

The information presenter 232 further comprises for contactless, wireless transfer of the monitored and/or stored data, a transponder which is adapted, to transfer, as is illustrated by the jagged arrow 226, the data to the data reception module 234 which belongs to the optical measurement apparatus, as is illustrated in FIG. 1.

In particular, the data reception module 234 is also equipped with a function of a transmitter, in order to transfer data to the information presenter 232, which may store the data in the storage module. In particular, the data reception module 234 is attached within a sample chamber 229 and is connected with the processing and control system 215 of the optical measurement apparatus. The data reception module 234 is in particular attached at an inner wall 227 of the sample chamber 229, the communication between the information presenter 232 and the data reception module 234 is performed wirelessly across a small air gap. Measurement values and/or storage data are transferred using the transponder module in the information presenter 232 to the data reception module 234 and the received data are forwarded to the processing and control system 215 for further processing and evaluation.

The measurement radiation 205 enters into the cuvette 230 along the optical axis 203 via a window 233, traverses or transmits the sample 117 within the cuvette 230, and exits from the cuvette 230 via the cuvette window 225 as changed measurement radiation 221. The measurement radiation 221 is, in an analogous way as described and explained with reference to FIG. 1, detected by an analysis section of an optical measurement apparatus and is evaluated together with the data evolving from the information presenter 232 using the processing and control system 215, such as to determine optical properties of the sample 117 or a concentration or/and a composition of the sample 117.

The cuvette 230 is held by a cuvette holder 226 and a correct positioning of the cuvette 230 may also be detected using the information presenter 232.

The energy supply of the energy needed for the reading or writing the data and/or operating the sensor is preferably transferred across the air transfer path, the transponder may be configured as a passive transponder.

For data transfer, beside the classical RFID, which transfers the data normally via a loss modulation to the transmitter coil, also a traditional radio transfer is employed. When enough energy has been transferred into the cuvette, it may be transmitted from there with every known radio method (e.g., ZigBee, WLAN, wireless USB, or the like).

The alternative utilization of active transponders having their own energy supply is also possible.

Figure 3:
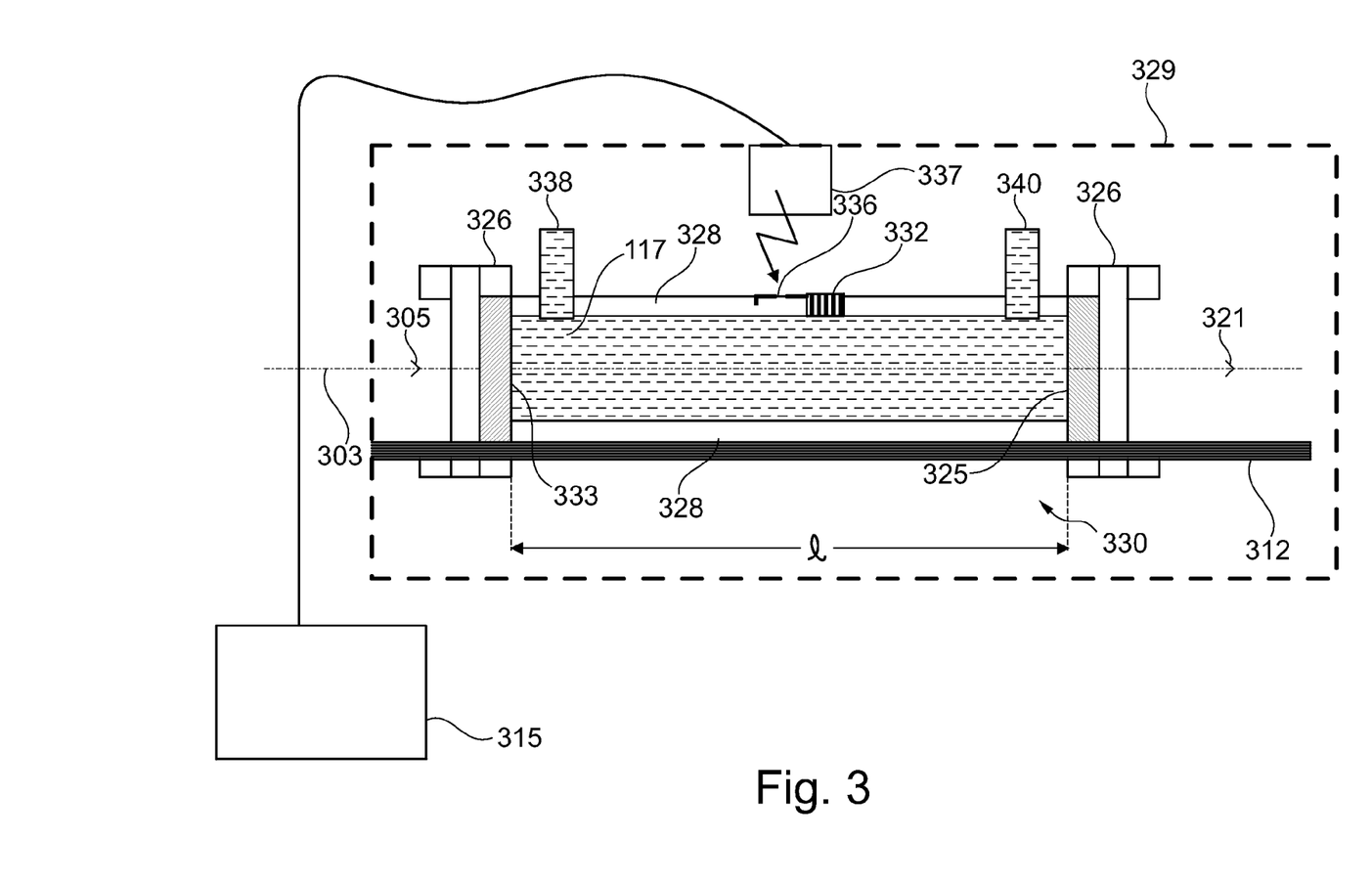
FIG. 3 schematically shows a cuvette according to an embodiment of the present invention, which may be in communication with components of the optical measurement arrangement as it is for example illustrated in FIG. 1.

FIG. 3 schematically illustrates a cuvette 330 according to an embodiment of the present invention, wherein a measurement of the temperature of the cuvette is performed in an optical manner using a pyrometer 337. At a section of the cuvette wall 328 a measurement window 336 is attached, which enables the optical measurement of the sample temperature within the cuvette 330. Thereby, the measurement may be performed directly via the infrared radiation which is emitted from the sample or the measurement may be performed via a fluorescence- and/or fluorescence decay time measuring, for example using a Rubin thermometer.

The cuvette 330 illustrated in FIG. 3 is configured as a flow through cuvette which comprises an inlet connector 338 and an outlet connector 340. Thereby, the sample 117 may be supplied via the inlet connector 338 into the sample reception space within the cuvette 330 and the sample may be discharged from the cuvette via the outlet connector 340.

The pyrometer 337 comprises a transmitter which can optically determine the temperature within the cuvette 330. Simultaneously, the cuvette data which are deposited in the information presenter 332 by way of an optical characterization carrier (for example adapted as bar code, colour code, etc.) may be read from the pyrometer 337 and may be forwarded via a data line to the processing and control system 315. Furthermore, FIG. 3 illustrates optical axis 303, measurement radiation 305, positioning arrangement 312, measurement radiation 321, holders 326, measurement assembly 329, cuvette window 325, cuvette window 333, and cuvette walls 328.

Figure 4:
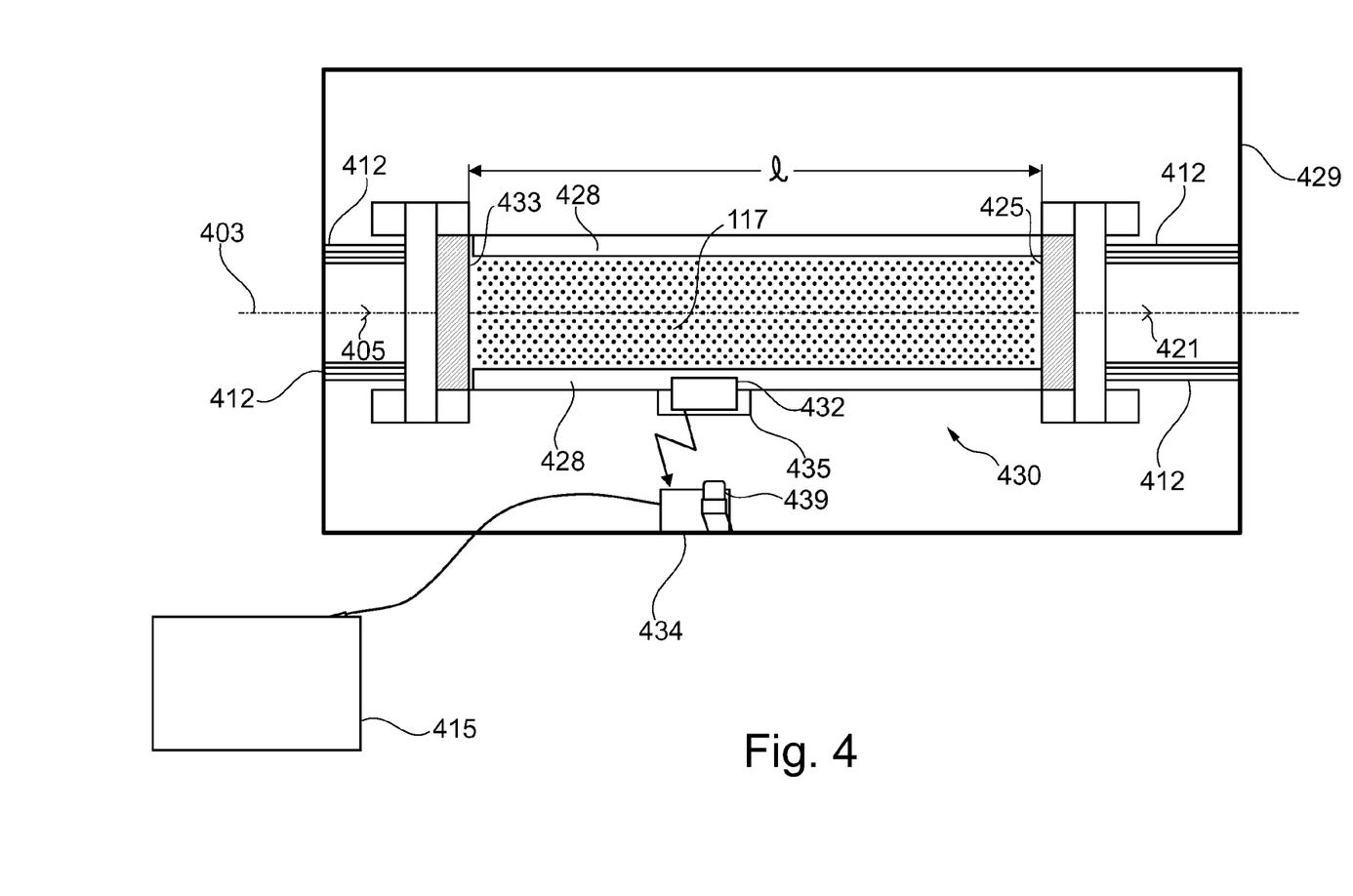
FIG. 4 shows a cuvette according to a further embodiment of the present invention, which may be in communication with components of the optical measurement apparatus illustrated in FIG. 1.

FIG. 4 schematically illustrates a cuvette 430 according to an embodiment of the present invention, which performs a wireless, contactless data transfer between an information presenter 432 and a data reception module 434 in an optical way. Further, also an energy supply of the information presenter 432 occurs in an optical way. Furthermore, FIG. 4 illustrates optical axis 403, measurement radiation 405, positioning arrangement 412, evaluation unit 415, measurement radiation 421, chamber 429, cuvette window 425, cuvette window 433, cuvette walls 428, and encapsulation 435.

The information provider or information presenter 432 comprises a storage and measurement unit, which is adapted for storing data and for measuring a temperature of the cuvette 430 or/and of the sample 117. The storage may contain cuvette data and/or calibration data. Further, the information presenter 432 includes a transmitter which converts the to be transferred data of the temperature sensor into an infrared signal and which radiates the infrared signal into the direction of the data reception module 434. Building upon the known IrDa-standard relatively high data throughputs upon low energy consumption and low error rates may be realized.

The data reception module 434 comprises besides an IR-reception module and a detector also an integrated LED 439 which may radiate energy for an energy supply of the information presenter 432. In particular, the light of the LED 439 is received from the information presenter 432 using the therein integrated photodiode and the electrical energy needed for the sensor operation and the transfer is extracted or gained therefrom. Optionally, a bidirectional, wireless transfer between the information presenter 432 and the data reception module 434 may occur, for example to enable programming the integrated storage in the information presenter 432 with the cuvette data.

In an alternative embodiment (not shown) a data transfer between the information presenter and the data reception module may be performed via a capacitive coupling of these two elements. Thereby, two electrodes may be closely adjacent to each other without mutually contacting. Thereby, an electrode plate may be encapsulated within the cuvette wall and may be electrically isolated from the electrode plate of the data reception module.

By a similar capacitive manner an energy transfer to the information presenter may occur.

According to an embodiment of the present invention data may be modulated onto the measurement beam using a coil formed around the measurement tube with a magnetic field using a Faraday effect. Thereby, the measurement radiation detector in the polarimeter may demodulate the signal. When the carrier frequency is correspondingly chosen this may not influence the polarimeter measurement. In the combination with the described energy transfer via the Faraday modulator coil the optical measurement apparatus would not require any additional hardware.

The invention claimed is:

1. Cuvette, comprising:
   a cuvette wall for limiting a sample reception space for receiving a fluid sample, wherein the cuvette wall is configured to allow a traversal of measurement radiation through the fluid sample situated within the sample reception space during an optical measurement;
   an information presenter for wirelessly providing data to be transferred to an external data reception module, wherein the data relate to the cuvette, wherein the data relate to an identification of the cuvette,
   wherein the information presenter is fixed at the cuvette wall,
   wherein the transferred data including the identification of the cuvette are usable by an evaluation unit of an optical measurement apparatus, to evaluate optical measurement data resulting from the optical measurement of the fluid sample situated within the sample reception space;
   wherein the information presenter comprises a sensor, which is configured to detect a physical quantity which relates to at least one of the sample and the cuvette, wherein the physical quantity is at least one of a temperature of the sample and a positioning of the cuvette, wherein the sensor is fixed at the cuvette wall, wherein the data to be transferred comprise measurement data, which are indicative for the physical quantity.

2. Cuvette according to claim 1, wherein the information presenter comprises an optical pattern.

3. Cuvette according to claim 1, wherein the information presenter comprises a data transfer module for electromagnetically transferring the data to be transferred.

4. Cuvette according to claim 3, wherein the data transfer module is configured for transferring the data to be transferred by using RF-technique, comprising at least one of Zigbee, WLAN and wireless USB, wherein the data transfer module comprises a transponder, which is one of active and passive.

5. Cuvette according to claim 1, wherein the data relating to the cuvette comprise data which relate to at least one of a geometry of the cuvette, a material of the cuvette wall, and calibration data of the sensor.

6. Cuvette according to claim 1, wherein the information presenter comprises an electronic storage, which is configured for storing of storage data and which is fixed at the cuvette wall, wherein the data to be transferred include at least a portion of the storage data.

7. Cuvette according to claim 6, further comprising a reception module for electromagnetically receiving at least one of data to be received and electrical energy for receiving.

8. Cuvette according to claim 7, which is configured to receive the electrical energy using RF-technique, comprising at least one of ZigBee, WLAN and wireless USB, and optically.

9. Cuvette according to claim 1, wherein the cuvette wall is at least 70% transparent along an optical axis of the measurement radiation, wherein the measurement radiation comprises a wavelength in at least a portion of a wavelength range between 300 nm and 1000 nm.

10. Cuvette according to claim 1, further comprising an inlet connection and an outlet connection which are arranged and configured to allow a supply of the sample from the inlet connection into the sample reception space, to allow a traversal of the sample through the sample reception space to the outlet connection and to allow a discharge of the sample out of the outlet connection.

11. Cuvette according to claim 1, wherein the information presenter is liquid-tightly encapsulated at the cuvette wall.

12. Cuvette according to claim 1, wherein the information presenter is fixed at the cuvette wall using at least one of an injection material and a casting material and a coating and welding.

13. Cuvette according to claim 1, wherein the information presenter is fixed at the cuvette wall such that the fixation sustains a cleaning using a tenside containing solution of a concentration between 0.5 wt % and 10 wt % at a temperature between 60° C. and 95° C., for a time range between 2 min and 30 min.

14. Optical measurement apparatus, comprising:
- a radiation source for generating a measurement radiation;
- a cuvette arranged in a radiation path of the measurement radiation, the cuvette having a cuvette wall for limiting a sample reception space for receiving a fluid sample, wherein the cuvette wall is configured to allow a traversal of measurement radiation through the fluid sample situated within the sample reception space;
- an information presenter fixed at the cuvette wall for wirelessly providing data to be transferred related to the cuvette, wherein the information presenter comprises a sensor configured to detect a physical quantity which relates to at least one of the sample and the cuvette, wherein the physical quantity is at least one of a temperature of the sample and a positioning of the cuvette, wherein the sensor is fixed at the cuvette wall, wherein the data to be transferred comprise measurement data, which are indicative for the physical quantity;
- a measurement radiation receiver which is arranged and configured to detect intensity values of the measurement radiation, which has traversed through the sample reception space of the cuvette;
- a data reception module which is configured for receiving the data of the information presenter, wherein the data relate to the cuvette; and
- an evaluation unit which is configured to evaluate the intensity values of the measurement radiation based on the received data which relate to the cuvette, to determine an optical property of a sample being situated within the sample reception space.

15. Optical measurement apparatus according to claim 14, which is configured as a polarimeter, wherein the optical property of the sample is indicative for an optical activity of the sample.

16. Optical measurement arrangement according to claim 14, wherein the received data relating to the cuvette comprise temperature data of the sample, wherein the evaluation unit is configured to determine the optical property of the sample upon taking into account the temperature data of the sample.

17. Optical measurement apparatus according to claim 14, further comprising at least one of a Faraday modulator and a Faraday compensator for changing a polarization direction of the measurement radiation, wherein the cuvette is configured to receive energy from an electromagnetic field generated by at least one of the Faraday modulator and the Faraday compensator.

18. Optical measurement arrangement according to claim 14, further comprising a pyrometer which is arranged and configured for detecting the temperature of the cuvette and which is communicatively coupled with the evaluation unit.

19. Optical measurement apparatus according to claim 14, wherein the cuvette is configured to modulate the data relating to the cuvette onto the measurement radiation and wherein the evaluation unit is configured for demodulating the modulated measurement radiation.

\* \* \* \* \*